United States Patent
Rodríguez Ropero et al.

(10) Patent No.: US 12,116,352 B2
(45) Date of Patent: Oct. 15, 2024

(54) PROCESS FOR PREPARING 1-DEOXY-1-METHYLAMINO-D-GLUCITOL 2-(3,5-DICHLOROPHENYL)-6-BENZOXAZOLECARBOXYLATE

(71) Applicant: INKE, S.A., Castellbisbal-Barcelona (ES)

(72) Inventors: Sergio Rodríguez Ropero, Castellbisbal-Barcelona (ES); Joan Huguet Clotet, Castellbisbal-Barcelona (ES)

(73) Assignee: INKE, S.A., Castellbisbal-Barcelona (ES)

( * ) Notice: Subject to any disclaimer, the term of this patent is extended or adjusted under 35 U.S.C. 154(b) by 470 days.

(21) Appl. No.: 17/601,946

(22) PCT Filed: Mar. 19, 2020

(86) PCT No.: PCT/EP2020/057683
§ 371 (c)(1),
(2) Date: Oct. 7, 2021

(87) PCT Pub. No.: WO2020/207753
PCT Pub. Date: Oct. 15, 2020

(65) Prior Publication Data
US 2022/0144787 A1    May 12, 2022

(30) Foreign Application Priority Data
Apr. 11, 2019 (EP) .................................... 19382273

(51) Int. Cl.
*C07D 263/57* (2006.01)

(52) U.S. Cl.
CPC .................................. *C07D 263/57* (2013.01)

(58) Field of Classification Search
CPC .................................................... C07D 263/57
See application file for complete search history.

(56) References Cited

U.S. PATENT DOCUMENTS

2015/0126567 A1   5/2015  Kandula
2019/0119226 A1   4/2019  Chen et al.

FOREIGN PATENT DOCUMENTS

| EP | 1587821 B1 | 8/2008 |
| WO | 2013/038351 A1 | 3/2013 |
| WO | 2013/168014 A1 | 11/2013 |
| WO | 2016/038500 A1 | 3/2016 |

OTHER PUBLICATIONS

Razavi et al., Benzoxazoles as transthyretin amyloid fibril inhibitors: synthesis, evaluation, and mechanism of action, Angew. Chem. Int. Ed. 2003, 42, 2758-2761.
Bulawa et al., Tafamidis, a potent and selective transthyretin kinetic stabilizer that inhibits the amyloid cascade, Proc. Natl Acad. Sci. USA, Early Edition, 2012, vol. 109, n° 24, 9629-9634.

*Primary Examiner* — Shawquia Jackson
(74) *Attorney, Agent, or Firm* — Casimir Jones, SC; Tristan A. Fuierer

(57) ABSTRACT

The present invention relates to an improved process for the preparation of 1-deoxy-1-methylamino-D-glucitol 2-(3,5-dichlorophenyl)-6-benzoxazolecarboxylate, also known as tafamidis meglumine. The process of the present invention is particularly suitable for industrial scale manufacture of tafamidis meglumine with excellent purity and high yields.

22 Claims, No Drawings

PROCESS FOR PREPARING 1-DEOXY-1-METHYLAMINO-D-GLUCITOL 2-(3,5-DICHLOROPHENYL)-6-BENZOXAZOLECARBOXYLATE

CROSS-REFERENCE TO RELATED APPLICATIONS

This application is filed under the provisions of 35 U.S.C. § 371 and claims the priority of International Patent Application No. PCT/EP2020/057683 filed on 19 Mar. 2020 entitled "PROCESS FOR PREPARING 1-DEOXY-1-METHYLAMINO-D-GLUCITOL 2-(3,5-DICHLOROPHENYL)-6-BENZOXAZOLECARBOXYLATE" in the name of Sergio RODRÍGUEZ ROPERO, et al., which claims priority to European Patent Application No. 19382273.1, filed on 11 Apr. 2019, both of which are hereby incorporated by reference herein in their entirety.

FIELD OF THE INVENTION

The present invention relates to an improved process for the preparation of 1-deoxy-1-methylamino-D-glucitol 2-(3,5-dichlorophenyl)-6-benzoxazolecarboxylate, also known as 6-carboxy-2-(3,5-dichlorophenyl)-benzoxazole meglumine or tafamidis meglumine. The process of the present invention is particularly suitable for industrial scale manufacture of tafamidis meglumine salt with high purity and high yields.

The present invention also relates to the potassium salt of 2-(3,5-dichlorophenyl)benzoxazole-6-carboxylate useful for the preparation of 6-carboxy-2-(3,5-dichlorophenyl)-benzoxazole meglumine in high yield and high purity.

The present invention also describes an improved process for the preparation of key intermediate methyl 4-(3,5-dichlorobenzamido)-3-hydroxybenzoate, suitable for industrial scale preparation of the product in high yield and high purity.

BACKGROUND OF THE INVENTION

6-Carboxy-2-(3,5-dichlorophenyl)-benzoxazole meglumine, compound of formula I (tafamidis meglumine), depicted below, is an orphan medicine used to delay nerve damage caused by transthyretin amyloidosis, a hereditary disease in which fibres called amyloid build up in tissues around the body including around the nerves. Tafamidis meglumine is commercialized under the trade name Vyndaqel by Pfizer.

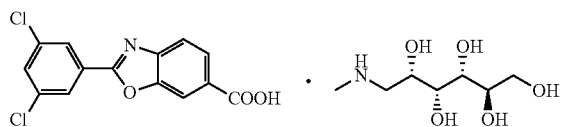

I

6-Carboxy-2-(3,5-dichlorophenyl)-benzoxazole (tafamidis free acid) was first disclosed in European patent EP 1 587 821 B1 in the name of Scripps Research Institute. EP 1 587 821 B1 describes in example 5 a synthetic approach for the preparation of tafamidis as shown in Scheme 1. The condensation of 4-amino-3-hydroxybenzoic acid with 3,5-dichlorobenzoyl chloride in the presence of pyridine in refluxing tetrahydrofuran furnishes 4-(3,5-dichlorobenzamido)-3-hydroxybenzoic acid, which without isolation, upon cyclization in the presence of p-toluensulphonic acid monohydrate in refluxing xylene, followed by methylation with $Me_3SiCHN_2$ in benzene/methanol affords methyl 2-(3,5-dichlorophenyl)benzo[d]oxazole-6-carboxylate, which finally, upon basic hydrolysis by means of $LiOH \cdot H_2O$ in tetrahydrofuran/methanol/$H_2O$ provides the free acid tafamidis as a white solid.

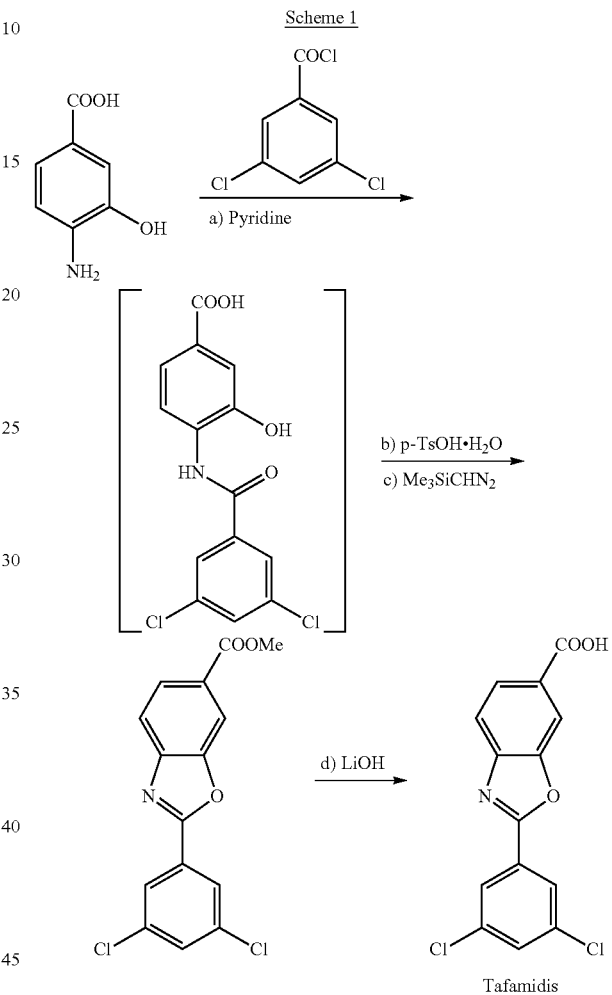

The process described in the aforementioned patent EP 1 587 821 B1 provides tafamidis free acid in low yields of 8%-27% over four steps. Additionally, toxic reagents and solvents such as pyridine and benzene and also dangerous reagents such as the diazomethane derivative $Me_3SiCHN_2$ are used. Purities are not disclosed.

Razavi et al. [Angew. Chem. Int. Ed. 2003, 42, 2758-2761] and WO 2013/168014 A1 disclose the preparation of tafamidis free acid involving the same four steps as shown in Scheme 1. Particularly, intermediate methyl 2-(3,5-dichlorophenyl)-benzoxazole-6-carboxylate and tafamidis free acid are purified by column chromatography. Yields and purities are not disclosed. This method presents some disadvantages such as purification by means of column chromatography, an unsuitable method for industrial scale applications.

Alternatively, Bulawa et. al. [Proceedings of the National Academy of Sciences of the USA, Early Edition, 2012, vol. 109, n° 24, 9629-9634] discloses the preparation of tafamidis free acid and tafamidis meglumine salt through key intermediate methyl 4-(3,5-dichlorobenzamido)-3-hydroxybenzoate, as shown in Scheme 2. Methyl 4-amino-3-hydroxybenzoate hydrochloride salt is reacted with 3,5-dichlorobenzoyl chloride in the presence of pyridine in dichloromethane to provide methyl 4-(3,5-dichlorobenzamido)-3-hydroxybenzoate which is further purified from acetone and water and isolated by filtration; then upon cyclization in the presence of p-toluensulphonic acid monohydrate affords methyl 2-(3,5-dichlorophenyl)benzo[d]oxazole-6-carboxylate, which is further isolated by filtration; and then reacted with LiOH in tetrahydrofuran/$H_2O$ (1:1 v/v) at 40-45° C. followed by pH adjustment with aqueous hydrochloric acid to yield the free acid tafamidis. This compound is further converted to the meglumine salt by reacting it with N-methyl-D-glucamine (also 1-deoxy-1-methylamino-D-glucitol) in a mixture of isopropyl alcohol/$H_2O$ at 65° C.-70° C., which is then isolated by filtration.

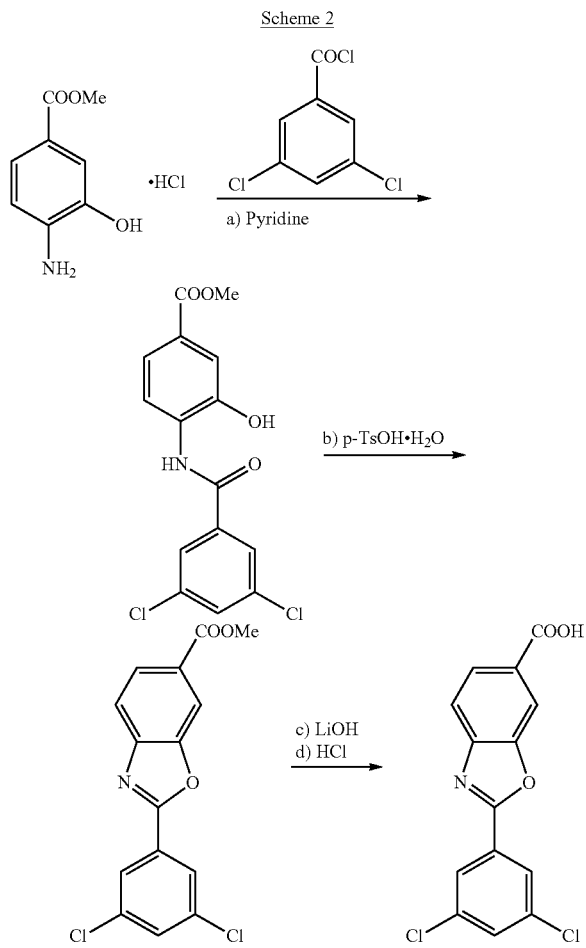

Scheme 2

Although the alternative process described by Bulawa et. al. avoids the use of dangerous diazomethane derivative such as $Me_3SiCHN_2$, toxic reagents such as pyridine are still used. Yields and purities are not disclosed.

WO 2016/038500 A1 discloses crystalline solid forms of tafamidis free acid (6-carboxy-2-(3,5-dichlorophenyl)-6-benzoxazole), referred as Form 1, Form 2, Form 4 and Form 6 and methods for their preparation. According to WO 2016/038500 A1, Form 1 is a non-hygroscopic, anhydrous crystalline solid form obtained by recrystallization from 2-propanol; Form 2 is a crystalline tetrahydrofuran solvate; Form 4 is another non-hygroscopic, anhydrous crystalline solid form obtained from a solvent (tetrahydrofuran)/antisolvent (toluene) crystallization method at low temperature (−10° C. to −25° C.) for 12 hours; Form 6 is other non-hygroscopic, anhydrous crystalline solid form obtained from a mixture of tetrahydrofuran/acetamide/dichloromethane at low temperature (about 0° C.). Generally, these crystallization processes carried out at low temperatures are not suitable for use at industrial scale. Purities are not disclosed.

Additionally, according to WO 2016/038500 A1 the tafamidis free acid obtained by reproducing the procedure of Razavi et al. (i.e. also described in EP 1 587 821 B1 and WO 2013/168014 A1) is essentially amorphous and physically unstable, thus, not suitable for use at industrial scale and most important not suitable for use in pharmaceutical preparations.

As already explained, to date the prior art failed to provide efficient methods for obtaining tafamidis meglumine salt in high purity and with high yields. The lack of efficient manufacturing processes increases the cost of the final tafamidis meglumine salt and the pharmaceutical compositions containing it, which has already resulted in expensive medications. In view of the pharmaceutical value of the compound of formula I, it is thus desirable to develop an efficient and safe process for the preparation of tafamidis meglumine salt in high purity and high yield, which can be easily applied at an industrial scale with low energy requirements and costs.

SUMMARY OF THE INVENTION

The present invention provides efficient and environmentally friendly processes for manufacturing 1-deoxy-1-methylamino-D-glucitol 2-(3,5-dichlorophenyl)-6-benzoxazolecarboxylate (tafamidis meglumine salt) allowing its preparation in high yield and high purity and applicable at industrial scale. The processes of the invention allow obtaining tafamidis meglumine salt without requiring laborious and unfeasible purification steps, yielding a high purity salt product, which complies with pharmaceutical standards.

In a first aspect, the present invention provides an improved process for preparing 1-deoxy-1-methylamino-D-glucitol 2-(3,5-dichlorophenyl)-6-benzoxazolecarboxylate, compound of formula I, comprising the steps of a) converting compound of formula II, wherein R is a $C_1$-$C_4$ alkyl and b) converting 6-carboxy-2-(3,5-dichlorophenyl)-6-benzoxazole of formula III into 1-deoxy-1-methylamino-D-glucitol 2-(3,5-dichlorophenyl)-6-benzoxazolecarboxylate of formula I, wherein step a) comprises the substeps of a1) treating the compound of formula II with a first inorganic base selected from the group consisting of sodium hydroxide and potassium hydroxide, in the presence of a first solvent or a first mixture of solvents to provide a compound of formula III wherein M is a cation selected from the group consisting of sodium and potassium and a2) treating the compound of formula IIIa obtained in substep a1) with an acid, preferably a hydracid such as hydrochloric acid, hydrobromic acid or hydroiodic acid, more preferably hydrochloric acid, to provide 6-carboxy-2-(3,5-dichlorophenyl)-6-benzoxazole of formula III as shown in Scheme 3. Through the use of said bases, it is possible to carry out the process without isolating tafamidis free acid, the compound of formula III (i.e. the process of the first aspect is carried out in one reaction vessel). Advantageously, the process of the invention provides 1-deoxy-1-methylamino-D-glucitol 2-(3,5-dichlorophenyl)-6-benzoxazolecarboxylate, compound of formula I, in high yield and high purity.

Scheme 3

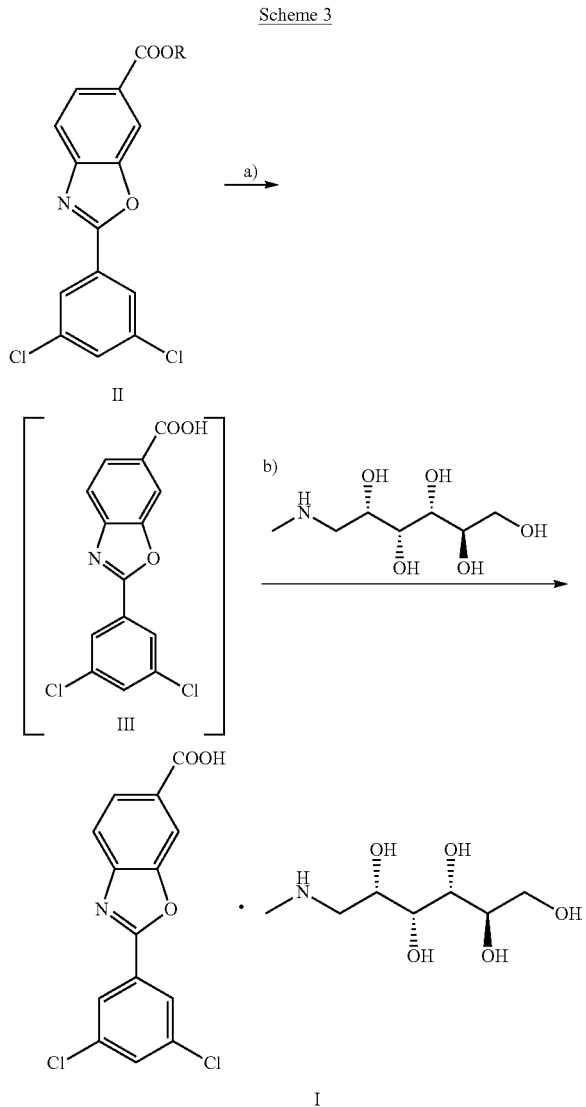

A second aspect of the present invention provides compounds of formula IIIa, wherein M is selected from the group consisting of sodium and potassium, preferably M is sodium

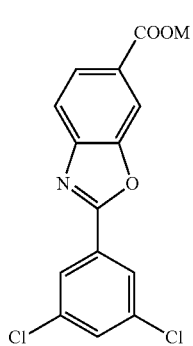

IIIa

A third aspect of the present invention relates to the use of compound IIIa, wherein M is selected from the group consisting of sodium and potassium, preferably M is sodium as an intermediate for the preparation of compound of formula I (tafamidis meglumine salt).

A fifth aspect of the present invention relates to a process for preparing a pharmaceutical composition comprising 1-deoxy-1-methylamino-D-glucitol 2-(3,5-dichlorophenyl)-6-benzoxazolecarboxylate, compound of formula I, said process comprising obtaining 1-deoxy-1-methylamino-D-glucitol 2-(3,5-dichlorophenyl)-6-benzoxazolecarboxylate of formula I following the process defined in the first aspect and combining said compound of formula I with at least one pharmaceutically acceptable carrier or excipient, optionally wherein said composition is adapted for use in the treatment of transthyretin amyloidosis.

Definitions

The term "one reaction vessel reaction" or "one reaction vessel process" is generally known in the art and refers to a chemical reaction wherein the starting material is converted to the end product of the reaction in a single reaction container, i.e. there is no intermediary reaction product which is isolated, removed or purified. A "one reaction vessel reaction" in its broadest meaning still allows the formation of intermediary products which are, however, further converted to the end-product by addition of further reactants (in situ generation of the intermediate). A one reaction vessel reaction also encompasses a reaction in a single reaction vessel where the starting product is converted to the end product through the formation of one or multiple intermediate products that are formed sequentially, even without further addition of a reagent ("multistep" reaction). Thus, a "one reaction vessel process" is characterized by at least two reaction steps carried out without isolation and/or purification of the intermediate product or products, and suitably carried out in a single reaction vessel/container. It will be understood by one of skill in the art that a simple transfer of the whole reaction mass at an intermediate stage, but without isolating and/or purifying the intermediate product, is still a "one reaction vessel process" according to the present invention, not the least because such a process would still achieve the technical advantage associated with a one reaction vessel process in that the intermediate formed in situ does not need to be isolated and/or purified.

The term "leaving group" as used herein refer to a molecular fragment that departs with a pair of electrons in heterolytic bond cleavage, in particular selected from the group consisting of acyl groups such as acetyl, sulfonate esters such as tosylate and mesylate and halogen atom such as fluorine, chlorine, bromine and iodine. Preferably the "leaving group" is an halogen such as Br, I or Cl, more preferably Cl.

The term "hydracid" (aka binary acid) as used herein refers to an inorganic acid in which hydrogen is combined with a second nonmetallic element such as S, F, Cl, Br or I. More preferably the "hydracid" is selected from the group consisting of hydrochloric acid, hydrobromic acid and hydroiodic acid.

As used herein the term "solvent" refers to a substance capable of at least partially dissolving another substance (i.e., the solute). Solvents may be liquids at room temperature. Solvents may be organic solvents (i.e. comprising at least one carbon atom) and water. In some embodiments, the solvent may be formed by the combination of two or more organic solvents, or by the combination of an organic solvent and water.

As used herein the term "organic solvent" refers to an organic molecule capable of at least partially dissolving another substance (i.e., the solute). Organic solvents may be liquids at room temperature. Examples of organic solvents that may be used for the present invention include, but are not limited to: hydrocarbon solvents (e.g., n-pentane, n-hexane, n-heptane, n-octane, paraffin, cyclohexane, methylcyclohexane, etc.) which also includes aromatic hydrocarbon solvents (e.g., benzene, toluene, o-xylene, m-xylene, and p-xylene); ester solvents (e.g., ethyl formate, methyl acetate, ethyl acetate, isopropyl acetate, butyl acetate, isobutyl acetate, ethyl malonate, etc.); ketone solvents (e.g., acetone, methyl ethyl ketone or 2-butanone, methyl isobutyl ketone, cyclohexanone, cyclopentanone, 3-pentanone, etc.); ether solvents (e.g., diethyl ether, dipropyl ether, diphenyl ether, isopropyl ether, tert-butyl methyl ether, tetrahydrofuran, 1,4-dioxane, etc.); alcohol solvents (e.g., methanol, ethanol, isopropanol, 1-propanol, 2-methyl-1-propanol, 1-butanol, 2-butanol, 1-pentanol, 3-methyl-1-butanol, tert-butanol, 1-octanol, benzyl alcohol, phenol, trifluoroethanol, glycerol, ethylene glycol, propylene glycol, m-cresol, etc.); acetonitrile. In some embodiments, the organic solvent may be formed by the combination of two or more organic solvents.

As used herein the term "protic solvent" refers to a solvent that contains a labile $H^+$, e.g. a hydrogen atom bound to an oxygen atom, to a nitrogen atom or to a fluorine atom. Examples of protic solvents are alcohol solvents (e.g., methanol, ethanol, isopropanol, 1-propanol, 2-methyl-1-propanol, 1-butanol, 2-butanol, 1-pentanol, 3-methyl-1-butanol, tert-butanol, 1-octanol, benzyl alcohol, phenol, trifluoroethanol, glycerol, ethylene glycol, propylene glycol, m-cresol, etc.), water, etc.

As used herein "alkyl" means straight-chain or branched hydrocarbon chain radical containing no insaturation having the indicated number of carbon atoms, such as from 1 to 10 carbon atoms, represented as $C_1$-$C_{10}$ alkyl. Such alkyl groups may be selected from methyl, ethyl, n-propyl, isopropyl, n-butyl, isobutyl, sec-butyl, tert-butyl, straight- or branched-pentyl, straight- or branched-hexyl, straight- or branched-heptyl, straight- or branched-nonyl or straight- or branched-decyl. Preferably the alkyl group is $C_1$-$C_4$ alkyl, more preferably the alkyl is methyl and ethyl.

The term "halogen" as used herein refer to an atom selected from the group consisting of fluorine, chlorine, bromine and iodine.

The term "inorganic base" as used herein refers to a substance that tends to accept a proton. It contains a metal cation and does not contain an organic moiety, as compared to an organic base, which is a substance that contains an organic moiety. Suitable inorganic bases for the present invention are hydroxides, carbonates or bicarbonates of an alkali metal such as lithium, sodium, potassium and caesium; or of an alkaline earth metal such as calcium and magnesium.

The terms "conventional isolation techniques" or "purification" as used herein refers to the process of rendering a product clean of foreign elements whereby a purified product can be obtained. The term "industrial purification" refers to purifications which can be carried out on an industrial scale such as solvent extraction, filtration, slurring, washing, phase separation, evaporation, centrifugation or crystallization. The term "conventional isolation techniques" as used herein refers to the process of separating a desired product from other (unwanted) components of the reaction mixture. Examples for conventional isolation techniques include, but are not limited to centrifugation, decantation, filtration, solvent evaporation, and the like.

The terms "conventional purification techniques" as used herein refer to the process of rendering a product (substantially) clean of unwanted elements, whereby a purified product can be obtained. Examples include but are not limited to solvent extraction (with or without phase separation), filtration, slurrying and crystallization/precipitation from a solvent or solvent mixture. Purification by chromatographic techniques is also "conventional", it is much less preferred in the industry in view of the typically low yields and high costs associated with this technique (due to, inter alia, large volumes of solvent and need for chromatography material) which often effectively prevents upscale of the process to an industrial scale.

As used herein, the term, "solvent extraction" refers to the process of separating components of a mixture by using a solvent which possesses greater affinity for one component and may therefore separate said one component from at least a second component which is less miscible than said one component with said solvent.

The term "filtration" refers to the act of removing solid particles greater than a predetermined size from a feed comprising a mixture of solid particles and liquid. The expression "filtrate" refers to the mixture without the solid particles removed by the filtration process. It will be appreciated that this mixture may contain solid particles smaller than the predetermined particle size. The expression "filter cake" refers to residual solid material remaining on a feed side of a filtration element.

The term "evaporation" refers to the change in state of solvent from liquid to gas and removal of that gas from the reactor or vessel. Various solvents may be evaporated during the synthetic route disclosed herein. As known to those of skilled in the art, each solvent may have a different evaporation time and/or temperature.

The term "phase separation" refers to a solution or mixture having at least two physically distinct regions.

As used herein, the term "slurrying" refers to any process which employs a solvent to wash, suspend or disperse a crude solid product.

The term "crystallization" refers to any method known to a person skilled in the art such as crystallization from single solvent or combination of solvents by dissolving the compound, optionally at elevated temperature and precipitating the compound by cooling the solution or removing solvent from the solution or both. It further includes methods such as dissolving the compound in a solvent and precipitating it by addition of an antisolvent (i.e. a solvent in which the desired compound has a lower solubility).

The term "high purity" as used herein refers to a purity of greater than 98%, or greater than 99%, or greater than 99.5%, or greater than 99.7%, or greater than 99.8%.

The term "high yield" as used herein refers to a yield of greater than 70%, or greater than 75%, or greater than 80%, or greater than 85%.

DETAILED DESCRIPTION OF THE INVENTION

According to the first aspect of the invention, herein is described and improved process for preparing 1-deoxy-1-methylamino-D-glucitol 2-(3,5-dichlorophenyl)-6-benzoxazolecarboxylate (tafamidis meglumine, compound of formula I)

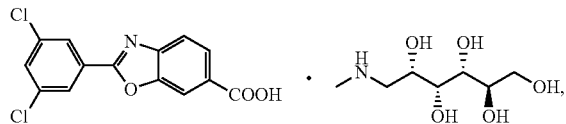

comprising the steps of:
a) converting a compound of formula II

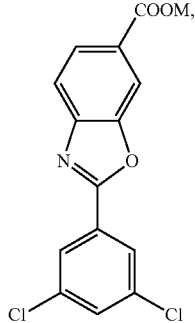

wherein R is a $C_1$-$C_4$ alkyl
into 6-carboxy-2-(3,5-dichlorophenyl)-6-benzoxazole, compound of formula III

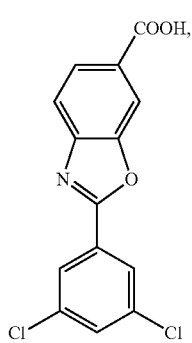

wherein step a) comprises the substeps of:
a1) treating the compound of formula II with a first inorganic base selected from the group consisting of sodium hydroxide and potassium hydroxide, in the presence of a first solvent or a first mixture of solvents to provide a compound of formula IIIa

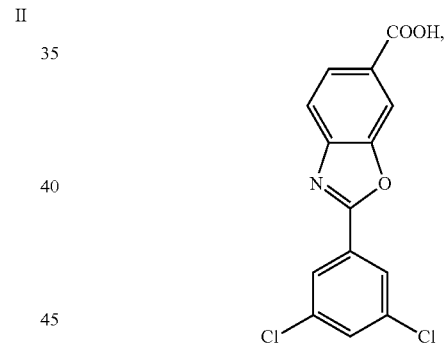

wherein M is a cation selected from the group consisting of sodium and potassium;
a2) treating the compound of formula IIIa obtained in substep a1) with an acid, preferably a hydracid such as hydrochloric acid, hydrobromic acid or hydroiodic acid, more preferably hydrochloric acid, to provide 6-carboxy-2-(3,5-dichlorophenyl)-6-benzoxazole of formula III b) converting compound of formula III obtained in step a) into 1-deoxy-1-methylamino-D-glucitol 2-(3,5-dichlorophenyl)-6-benzoxazolecarboxylate, compound of formula I.

The use of sodium or potassium hydroxide as the first inorganic base allows carrying out the process without isolation of compound of formula III.

The present inventors have realized that tafamidis free acid, compound of formula III, precipitates in the reaction media just after the addition of an aqueous hydrochloric acid when reproducing the process as described by Bulawa et. al. Therefore, the tafamidis free acid obtained is isolated from the reaction media by filtration and is further converted to the meglumine salt. On the other hand, the present inventors have surprisingly found that compound of formula I, can be prepared through the steps a) and b) according to the process of the first aspect in one single reaction vessel. The point is that Tafamidis free acid, compound of formula III, prepared according to the first aspect is not isolated, since it does not precipitate in the reaction media. Advantageously, the process of the invention according to the first aspect provides 1-deoxy-1-methylamino-D-glucitol 2-(3,5-dichlorophenyl)-6-benzoxazolecarboxylate, compound of formula I, in high yield and high purity.

Advantageously, the process of the present invention avoids the isolation of advanced intermediates, the compounds of formula IIIa and compound of formula III, and therefore, reduces the number of steps to provide 1-deoxy-1-methylamino-D-glucitol 2-(3,5-dichlorophenyl)-6-benzoxazolecarboxylate, the compound of formula I and this constitutes a preferred embodiment of the invention.

In another embodiment of the first aspect of the present invention, step a) further comprises an additional substep a3) of adding water to the resulting mixture obtained after the substep a2). The amount of water (by volume, in millilitres) may be of from 1:1 (v/w) to 10:1 (v/w), preferably is of from 1:1 (v/w) to 5:1 (v/w) with respect to the weight (in grams) of the compound of formula II treated in stage a1).

In another embodiment of the first aspect of the present invention, step a) comprises substep a3) as described in the previous paragraph followed by an additional substep a4) of decanting the resulting mixture obtained in substep a3) to separate the aqueous phase (mainly containing inorganic salts) from the desired organic phase (mainly containing compound of formula III), followed by discarding the aqueous phase.

Advantageously, the separation of the inorganic salts obtained in substep a2), which are by-product impurities, from compound of formula III allows the following step b) of the first aspect of the present invention, the meglumine salt formation, since the competition of salt formation are significantly reduced, and consequently, not only increases the overall yield of the process, but also the purity of compound of formula I.

In another embodiment of the first aspect the first solvent or first mixture of solvents used in substep a1) is a mixture of an organic solvent and water. Suitable organic solvents may be selected from the group consisting of ethers, alcohols and mixtures thereof. Suitable ethers include diethyl ether, tert-butyldimethyl ether, tetrahydrofuran, dioxane and mixtures thereof. Suitable alcohols include linear, cycled or branched $C_1$-$C_6$ alcohols, preferably methanol, ethanol, n-propanol, n-butanol, iso-propanol and mixtures thereof. Preferably, the first solvent or first mixture of solvents used in substep a1) is a mixture of an ether and water, more preferably the solvent used in substep a1) is a mixture of tetrahydrofuran and water.

In another embodiment of the first aspect, the ratio (by volume) of tetrahydrofuran to water used in substep a1) is in the range of from 2:1 (v/v) to 15:1 (v/v), preferably of from 5:1 (v/v) to 10:1 (v/v), more preferably of from 6:1 (v/v) to 8:1 (v/v).

In another embodiment of the first aspect, the process substep a1) may be conducted at a temperature range of from 40° C. to 70° C., preferably of from 45° C. to 65° C., more preferably of from 50° C. to 60° C.

In another embodiment of the first aspect, the acid used in substep a2) according to the first aspect of the present invention is an inorganic or an organic acid. Suitable acids are those which have a pKa (relative to water) below 5, preferably below 3, more preferably below 1. Preferably, the acid has a pKa (relative to water) from −10 to 5, preferably from −10 to 3, more preferably from −10 to 1. Examples of suitable acids include but are not limited to hydrofluoric acid, hydrochloric acid, hydrobromic acid, phosphoric acid, sulfuric acid, formic acid, acetic acid, dichloroacetic acid, methansulfonic acid, p-toluensulfonic acid and camphorsulfonic acid. Preferably, the acid is a hydracid such as hydrochloric, hydrobromic or hydroiodic acid, which may be present either as gas or as an aqueous solution or generated in situ, for example from an alkylsilyl halogenide in the presence of a protic solvent.

In a preferred embodiment of the first aspect, the acid used in substep a2) is hydrochloric acid. The molar ratio of the compound of formula IIIa to the acid is from 1:1 to 1:3. Preferably, the molar ratio of compound of formula IIIa to the acid is from 1:1 to 1:1.5.

In another preferred embodiment of the first aspect, the process substep a2) may be conducted at a temperature range of from 35° C. to 70° C., preferably of from 40° C. to 60° C., more preferably of from 45° C. to 55° C.

In another preferred embodiment of the first aspect, the process substep a3) may be conducted at a temperature range of from 35° C. to 70° C., preferably of from 40° C. to 60° C., more preferably of from 45° C. to 55° C.

In another preferred embodiment of the first aspect, the process substep a4) may be conducted at a temperature range of from 35° C. to 70° C., preferably of from 40° C. to 60° C., more preferably of from 45° C. to 55° C.

In another embodiment of the first aspect of the present invention, R is selected from the group consisting of methyl and ethyl, preferably R is methyl.

In another embodiment of the first aspect, the cation M is sodium. Accordingly, the hydroxide of an alkali metal used in substep a1) is sodium hydroxide.

In a preferred embodiment of the first aspect, the process for preparing compound of formula I comprises the following steps and substeps:

a1) reacting the compound of formula II, wherein R is methyl with an hydroxide of an alkali metal selected from the group consisting of sodium hydroxide and potassium hydroxide in the presence of a first solvent or a first mixture of solvents to provide the compound of formula IIIa

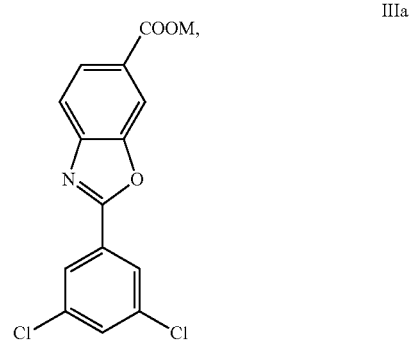

wherein M is selected from the group consisting of sodium and potassium a2) adding hydrochloric acid to the compound of formula IIIa obtained in substep a1) to provide tafamidis free acid, compound of formula III

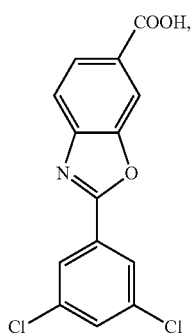

a3) adding water to the resulting mixture obtained in substep a2), a4) decanting the resulting mixture obtained in substep a3) followed by discarding the resulting aqueous phase, and step b) converting the compound of formula III into 1-deoxy-1-methylamino-D-glucitol 2-(3,5-dichlorophenyl)-6-benzoxazolecarboxylate, compound of formula I, wherein the compounds of formula IIIa and 6-carboxy-2-(3,5-dichlorophenyl)-6-benzoxazole of formula III are not isolated (i.e. the process is carried out in one reaction vessel).

In another embodiment of the first aspect, the process step b) comprises converting compound of formula III obtained in step a) into 1-deoxy-1-methylamino-D-glucitol 2-(3,5-dichlorophenyl)-6-benzoxazolecarboxylate, compound of formula I, in the presence of a second solvent or a second mixture of solvents.

In a further embodiment of the first aspect, the process step b) comprises the substeps of:

b1) adding N-methyl-D-glucamine (1-deoxy-1-methylamino-D-glucitol) to compound of formula III obtained in step a), b2) removing the solvent of the resulting mixture obtained in substep b1), preferably by distillation, and b3) treating the resulting mixture obtained in substep b2) with a second solvent or a second mixture of solvents.

The process of adding N-methyl-D-glucamine to compound of formula III is carried out at the end of step a), in particular after substep a2) or after the last one of substeps a3) and a4) when these substeps are performed. Preferably substep a4) is carried out and N-methyl-D-glucamine is added to compound III obtained in substep a4).

The solvent or mixture of solvents present in the mixture obtained in substep b1) is the solvent present at the end of step a). In particular, the solvent or mixture of solvents present in the last substep performed from substeps a1), a2), a3) and/or a4).

In one embodiment of the first aspect, the second solvent or second mixture of solvents used in substep b3) may be a mixture of an organic solvent and water. Suitable organic solvents may be selected from alcohols, ethers, esters, ketones and mixtures thereof, preferably the organic solvent is selected from the group consisting of alcohols and ethers. Suitable alcohols include linear, cycled or branched $C_1$-$C_6$ alcohols, preferably methanol, ethanol, isopropanol and mixtures thereof. Suitable ethers include diethyl ether, tert-butyldimethyl ether, tetrahydrofuran, dioxane and mixtures thereof. Suitable esters include ethyl acetate, isopropyl acetate and mixtures thereof. Suitable ketones include acetone, methyl isobutylketone and mixtures thereof. Preferably, the solvent or mixture of solvents used in substep b3) is a mixture of an alcohol and water. More preferably, the alcohol is selected from the group consisting of methanol, ethanol and isopropanol. More preferably the alcohol is isopropanol.

In another embodiment of the first aspect, the process step b) may be conducted at a temperature range of from 30° C. to 70° C., preferably of from 40° C. to 50° C., more preferably at 45° C.

In another preferred embodiment of the first aspect, the process substeps b1), b2) and/or b3) may be conducted at a temperature range of from 30° C. to 70° C., preferably of from 40° C. to 50° C., more preferably at 45° C.

In another embodiment of the first aspect, the process further comprises isolating compound of formula I, preferably by means of conventional isolating techniques, more preferably by filtration.

In another embodiment of the first aspect, the process further comprises purifying compound of formula I, preferably by means of conventional purification techniques, more preferably by crystallization.

In another preferred embodiment of the first aspect, the process for preparing compound of formula I comprises the following steps and substeps:

a1) reacting the compound of formula II, wherein R is methyl with an hydroxide of an alkali metal selected from the group consisting of sodium hydroxide and potassium hydroxide in the presence of a first solvent or a first mixture of solvents to provide the compound of formula IIIa

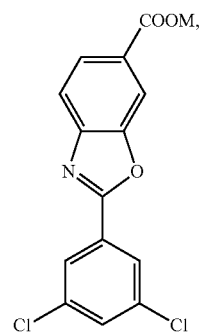

wherein M is selected from the group consisting of sodium and potassium a2) adding hydrochloric acid to the compound of formula IIIa obtained in substep a1) to provide tafamidis free acid, compound of formula III

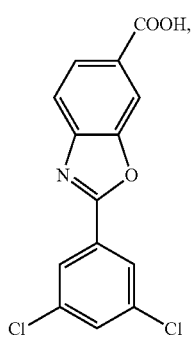

III a3) adding water to the resulting mixture obtained in substep a2), a4) decanting the resulting mixture obtained in substep a3) followed by discarding the resulting aqueous phase, and step b) of converting the compound of formula III into 1-deoxy-1-methylamino-D-glucitol 2-(3,5-dichlorophenyl)-6-benzoxazolecarboxylate, compound of formula I, comprising the substeps of:

b1) adding N-methyl-D-glucamine (1-deoxy-1-methylamino-D-glucitol) to compound of formula III obtained in substep a4) to provide compound of formula I, b2) removing the solvent of the resulting mixture obtained in substep b1), preferably by distillation, and b3) treating the resulting mixture obtained in substep b2) with a second solvent or a second mixture of solvents;

wherein the compounds of formula IIIa and 6-carboxy-2-(3,5-dichlorophenyl)-6-benzoxazole of formula III are not isolated (i.e. the process is carried out in one reaction vessel).

In another more preferred embodiment of the first aspect, the process for preparing compound of formula I comprises the following steps and substeps:

a1) reacting the compound of formula II, wherein R is methyl;

with an hydroxide of an alkali metal selected from the group consisting of sodium hydroxide and potassium hydroxide in the presence of tetrahydrofuran and water to provide the compound of formula IIIa,

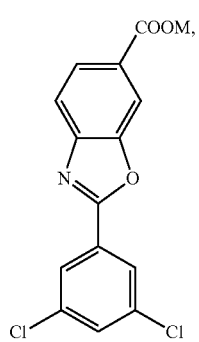

IIIa wherein M is selected from the group consisting of sodium and potassium a2) adding hydrochloric acid to the compound of formula IIIa obtained in substep a1) to provide tafamidis free acid, compound of formula III,

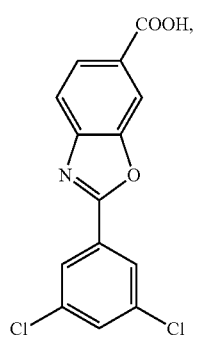

III a3) adding water to the resulting mixture obtained in substep a2), a4) decanting the resulting mixture obtained in substep a3) followed by discarding the resulting aqueous phase, and step b) of converting the compound of formula III into 1-deoxy-1-methylamino-D-glucitol 2-(3,5-dichlorophenyl)-6-benzoxazolecarboxylate, compound of formula I, comprising the substeps of:

b1) adding N-methyl-D-glucamine (1-deoxy-1-methylamino-D-glucitol) to compound of formula III obtained in substep a4) to provide compound of formula I, b2) removing the solvent of the resulting mixture obtained in substep b1), preferably by distillation, and b3) treating the resulting mixture obtained in substep b2) with a second solvent or a second mixture of solvents;

wherein the compounds of formula IIIa and 6-carboxy-2-(3,5-dichlorophenyl)-6-benzoxazole of formula III are not isolated (i.e. the process is carried out in one reaction vessel).

Substeps a1), a2) a3 and a4) may be carried out as previously described herein.

Subteps b1), b2) and b3) may be carried out as previously described herein.

The second aspect provides the compound of formula IIIa, wherein M is selected from the group consisting of sodium and potassium, preferably M is potassium. Advantageously, the potassium salt of compound IIIa (potassium salt of 2-(3,5-dichlorophenyl)benzoxazole-6-carboxylate) is particularly useful for the preparation of 1-deoxy-1-methylamino-D-glucitol 2-(3,5-dichlorophenyl)-6-benzoxazolecarboxylate, compound of formula I, in high yield and high purity.

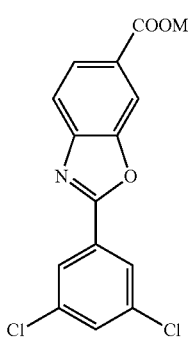

IIIa

The inventors have realized that compound of formula IIIa, wherein M is a cation selected from lithium, compete with the meglumine salt in the corresponding salt formation process precipitating the lithium salt of compound IIIa instead of the meglumine salt. Surprisingly, compound of formula IIIa, wherein M is potassium or sodium, the potassium 2-(3,5-dichlorophenyl)benzoxazole-6-carboxylate or sodium 2-(3,5-dichlorophenyl)benzoxazole-6-carboxylate, remain soluble in the reaction media and there is no competition at the time of precipitating the meglumine salt. Therefore, the compound IIIa, wherein M is potassium or sodium, preferably the compound wherein M is sodium, are particularly useful for the preparation of 1-deoxy-1-methylamino-D-glucitol 2-(3,5-dichlorophenyl)-6-benzoxazolecarboxylate, compound of formula I, in high yield and high purity, due to its higher solubility in the reaction media when compared to the corresponding known lithium salt of compound IIIa.

The third aspect of the present invention relates to the use of compound IIIa, wherein M is selected from the group consisting of sodium and potassium, as an intermediate for the preparation of compound of formula I (tafamidis meglumine salt).

The fourth aspect of the present invention provides a process for the preparation of a compound of formula II, wherein R is a $C_1$-$C_4$ alkyl,

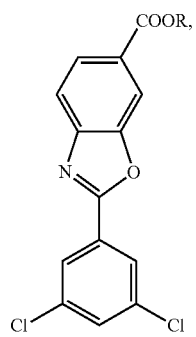

II comprising the steps of:
i) reacting a compound of formula V,

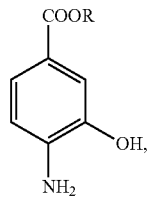

V wherein R is $C_1$-$C_4$ alkyl,
with a compound of formula VI,

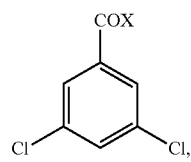

VI wherein X is a leaving group, preferably a halogen, more preferably X is chloride,
in the presence of a second inorganic base and in a third solvent or a third mixture of solvents to provide compound of formula IV,

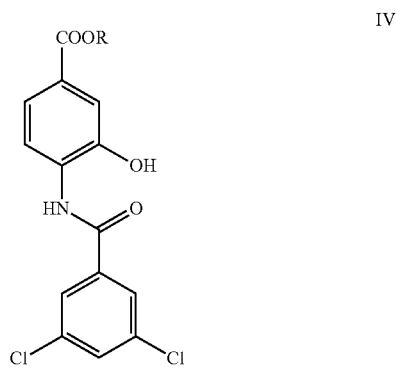

IV wherein R is as defined above, and
ii) converting the compound of formula IV into the compound of formula II.

In one embodiment of the fourth aspect, R is selected from the group consisting of methyl and ethyl, preferably methyl.

In another embodiment of the fourth aspect, the second inorganic base is an alkali metal carbonate or bicarbonate, preferably selected form the group consisting of sodium carbonate, sodium bicarbonate, potassium carbonate and potassium bicarbonate, more preferably sodium bicarbonate.

In another embodiment of the fourth aspect, the third solvent is tetrahydrofuran, or the third mixture of solvents comprises tetrahydrofuran, preferably the third solvent is tetrahydrofuran.

In another embodiment of the fourth aspect, the process further comprises isolating compound of formula IV, preferably by means of conventional isolating techniques, more preferably by filtration.

In another embodiment of the fourth aspect, the process further comprises purifying compound of formula IV, preferably by means of conventional purification techniques, more preferably by crystallization.

The compound of formula IV may be converted into the compound of formula II as described in prior art (e.g. Bulawa et. al. [Proceedings of the National Academy of Sciences of the USA, Early Edition, 2012, vol. 109, n° 24, 9629-9634). In particular, compound IV may be cycled in the presence of p-toluensulfonic acid in toluene (preferably at reflux temperature), and optionally followed by treatment with charcoal, to afford the corresponding 2-(3,5-dichlorophenyl)-6-benzoxazolecarboxylate of formula II. In a preferred embodiment, compound of formula II thus obtained is purified in a mixture of acetone and water.

A fifth aspect of the invention relates to a process for preparing a pharmaceutical composition comprising tafamidis or a pharmaceutically acceptable salt thereof, preferably tafamidis meglumine, said process comprising obtaining 1-deoxy-1-methylamino-D-glucitol 2-(3,5-dichlorophenyl)-6-benzoxazolecarboxylate of formula I following the process defined in the first aspect and further combining said tafamidis or a pharmaceutically acceptable salt thereof with at least one pharmaceutically acceptable carrier or excipient; optionally wherein the pharmaceutical composition is adapted for use in the treatment of transthyretin amyloidosis.

Having described the various aspects of the present invention in general terms, it will be apparent to those of skill in the art that many modifications and slight variations are possible without departing from the spirit and scope of the present invention. The present invention is now further illustrated by the following working examples. They should in no case be interpreted as a limitation of the scope of the invention as defined in the claims. Unless indicated otherwise, all indications of percentage are by weight and temperatures are in degrees Celsius.

Experimental

The compounds of the present invention were characterized by common analytical techniques such as $^1$H-NMR or $^{13}$C-NMR, IR spectrometry (Perkin Elmer FTIR Spectrum One appliance using a Perkin Elmer ATR accessory), Differential Scanning Calorimetry (DSC) and PXRD (Powder X-Ray Diffraction) using the following methods:

DSC analyses were recorded in a Mettler Toledo DSC822e calorimeter. Experimental conditions: 40 µL aluminum crucibles; atmosphere of dry nitrogen at 50 mL/min flow rate; heating rate of 10° C./min between 30 and 300° C. Data collection and evaluation was done with software STARe.

PXRD analyses were acquired on a D8 Advance Series 2Theta/Theta powder diffraction system using CuKα1-radiation (λ=1.54056 Å) in transmission geometry. The system is equipped with a VÅNTEC-1 single photon counting PSD, a Germanium monochromator, a ninety positions auto changer sample stage, fixed divergence slits and radial soller. The sample was measured in a 60 minute scans in a range from 4° to 40° in 2θ. Programs used: Data collection with DIFFRAC plus XRD Commander V.2.5.1 and evaluation with EVA V.12.0.

EXAMPLES

Reference Example 1: Preparation of methyl 4-(3,5-dichlorobenzamido)-3-hydroxybenzoate To a suspension of methyl 4-amino-3-hydroxybenzoate (2.0 g, 12.0 mmol) in dry CH$_2$Cl$_2$ (20 mL) was added, at a temperature of 20-25° C., pyridine (1.2 mL, 15.0 mmol). The mixture was cooled down to a temperature of 0-5° C. and maintained for 15 min. Then, a solution of 3,5-dichlorobenzoyl chloride (2.7 g, 12.6 mmol) was added. The resulting suspension was warmed at a temperature of 20-25° C. and the reaction was stirred for 16 hours. Once the reaction was finished, the thick suspension was filtered and washed with CH$_2$Cl$_2$. The obtained brown solid was suspended in a mixture of acetone/H$_2$O and the slurry was stirred for an hour at room temperature; the solid was filtered, washed with a mixture of acetone and water and dried in an air-oven at 45° C. affording methyl 4-(3,5-dichlorobenzamido)-3-hydroxybenzoate (2.46 g, 7.2 mmol) as a light brown solid which was slightly impurified by TLC.
Yield: 60%

Example 1: Synthesis of methyl 4-(3,5-dichlorobenzamido)-3-hydroxybenzoate

To a suspension of methyl 4-amino-3-hydroxybenzoate (50.0 g, 300 mmol) in of dry THF (400 mL) was added, at a temperature of 20-25° C., NaHCO$_3$ (27.6 g, 330 mmol). The mixture was cooled down to a temperature of 10-15° C. and a solution of 3,5-dichlorobenzoyl chloride (65.8 g, 314 mmol) in of dry THF (100 mL) was added dropwise maintaining the internal temperature below 20° C. Then, the temperature was adjusted to 20-25° C. and the reaction mixture was stirred for 16 hours. Once the reaction was finished, the solvent was vacuum distilled, and the resulting crude was resuspended in 500 mL of a mixture of acetone (250 mL) and water (250 mL). The thick suspension was stirred at room temperature for an hour and at 0-5° C. for an hour more. The obtained solid was filtered, washed with a mixture of acetone and water, and dried in an air-oven at 45° C. affording methyl 4-(3,5-dichlorobenzamido)-3-hydroxybenzoate (93.4 g, 275 mmol) as a light brown solid.
Yield: 91.8%

Example 2: Synthesis of methyl 2-(3,5-dichlorophenyl)benzo[d]oxazole-6-carboxylate p-Toluenesulfonic acid monohydrate (4.5 g, 23.52 mmol) was added to a suspension of methyl 4-(3,5-dichlorobenzamido)-3-hydroxybenzoate (80 g, 235.2 mmol), obtained in example 1, in toluene (1.6 L). The resulting mixture was heated at reflux and the reaction was stirred for 16 hours with elimination of water. The solution was cooled down to 45° C. and filtered. Solvent was vacuum distilled, and the resulting crude was resuspended in acetone (560 mL) and water (80 mL). The resulting thick suspension was stirred at room temperature for an hour, the solid was filtered, washed with a mixture of acetone and water and dried in an air-oven at 45° C. furnishing methyl 2-(3,5-dichlorophenyl)benzo[d]oxazole-6-carboxylate (70.0 g, 217.0 mmol) as a slightly brown solid.
Yield: 92.4%

Example 3: Preparation of 1-deoxy-1-methylamino-D-glucitol 2-(3,5-dichlorophenyl)-6-benzoxazolecarboxylate (tafamidis meglumine)

To a suspension of methyl 2-(3,5-dichlorophenyl)benzo[d]oxazole-6-carboxylate (2.0 g, 6.21 mmol) in THF (40 mL) at 50-55° C. was added a solution of KOH (533 mg, 8.07 mmol) in water (6 mL). The resulting orange solution was stirred for 3 hours, cooled down to 45° C., and neutralized with an aqueous solution of 6M HCl at 45° C. Water (10 mL) was added at 45° C., and the phases were separated at 45° C. discarding the aqueous phase. Meglumine (1.27 g, 6.52 mmol) was added at 45° C. and the solvent was vacuum distilled. Ethanol (40 mL) and water (4 mL) were added to the crude. The resulting suspension was heated at 45° C., stirred for 30 min, and slowly cooled down to room temperature. The resulting suspension was stirred at room temperature for an hour, the solid was filtered, washed with a mixture of ethanol and water and dried in an air-oven at 45° C. furnishing tafamidis meglumine (2.60 g, 5.17 mmol) as an off-white solid.
Yield: 83.2%

Purity by HPLC: 99.70%

DSC: Endothermic peak due to the melting at 198.6° C. (-155 J/g).

The PXRD pattern corresponds to that disclosed in FIG. 1A of WO 2013/038351 A1.

Example 4: Preparation of 1-deoxy-1-methylamino-D-glucitol 2-(3,5-dichlorophenyl)-6-benzoxazolecarboxylate (tafamidis meglumine)

To a suspension of methyl 2-(3,5-dichlorophenyl)benzo[d]oxazole-6-carboxylate (60.0 g, 186.3 mmol) in THF (1200 mL) at 50-55° C. was added a solution of KOH (16.0 g, 242.1 mmol) in water (180 mL). The resulting orange solution was stirred for 3 hours, cooled down to 45° C., and neutralized with an aqueous solution of 6M HCl at 45° C. Water (300 mL) was added at 45° C., and the phases were separated at 45° C. discarding the aqueous phase. Meglumine (38.2 g, 186.3 mmol) was added at 45° C. and the solvent was vacuum distilled. Ethanol (1200 mL) and water (120 mL) were added to the crude. The resulting suspension was heated at 45° C., stirred for 30 min, and slowly cooled down to room temperature. The resulting suspension was stirred at room temperature for an hour, the solid was filtered, washed with a mixture of ethanol and water and dried in an air-oven at 45° C. furnishing tafamidis meglumine (80.9 g, 161.0 mmol) as an off-white solid.

Yield: 86.3%

Example 5: Preparation of 1-deoxy-1-methylamino-D-glucitol 2-(3,5-dichlorophenyl)-6-benzoxazole carboxylate (tafamidis meglumine)

To a suspension of methyl 2-(3,5-dichlorophenyl)benzo[d]oxazole-6-carboxylate (2.0 g, 6.21 mmol) in THF (40 mL) at 50-55° C. was added a solution of LiOH·H$_2$O (340 mg, 8.07 mmol) in water (6 mL). The resulting yellow solution was stirred for 3 hours, cooled down to 45° C., and neutralized with 6M aqueous HCl. Then, a solution of 1% aqueous NaCl (10 mL) was added at 45° C.-50° C., and the phases were separated discarding the aqueous phase. Meglumine (1.27 g, 6.52 mmol) was added at 45° C.-50° C. and the solvent was vacuum distilled. Ethanol (40 mL) and water (4 mL) were added to the crude. The resulting suspension was heated at 45° C., stirred for 30 min, and slowly cooled down to room temperature. The suspension was stirred at room temperature for an hour, filtered off, washed with a mixture of ethanol and water and dried in an air-oven at 45° C. furnishing tafamidis meglumine (2.20 g, 4.37 mmol) as an off-white solid.

Yield: 70.4%

Example 6: Preparation of 1-deoxy-1-methylamino-D-glucitol 2-(3,5-dichlorophenyl)-6-benzoxazole carboxylate (tafamidis meglumine)

A suspension of 30.0 g (93.13 mmol) of methyl 2-(3,5-dichlorophenyl)benzo[d]oxazole-6-carboxylate of formula II in 600 mL of THF was heated at 50-55° C. Then, NaOH (4.16 g, 102.4 mmol) in 90 mL of water was added. The resulting orange solution was stirred for 6 h and neutralized with HCl 6M. Water (150 mL) was added, and the phases were separated discarding the aqueous phase. Meglumine (19.09 g, 97.8 mmol) was added and the solvent was vacuum distilled. Isopropanol (600 mL) and water (150 mL) were added to the crude. The resulting suspension was heated to 65° C., stirred for 30 min, and slowly cooled down to room temperature. The suspension was stirred at room temperature for 6 h, the solid was filtered, washed with a mixture of IPA/H2O and dried in an air-oven at 45° C. furnishing Tafamidis meglumine (38.9 g, 77.3 mmol) as a white off solid (SRR-TAF-148-1)

Yield: 83.0%

HPLC purity: 99.87%

DRX: form M

The invention claimed is:

1. A process for preparing 1-deoxy-1-methylamino-D-glucitol 2-(3,5-dichlorophenyl)-6-benzoxazolecarboxylate of formula I,

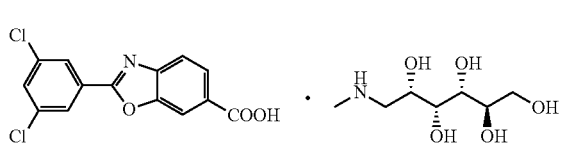

comprising the steps of:
a) converting a compound of formula II

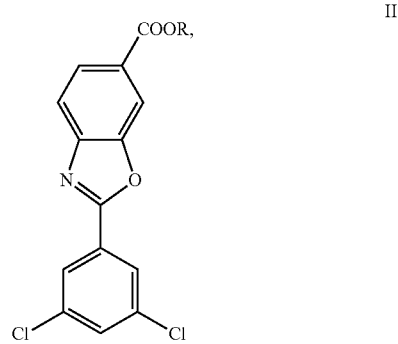

wherein R is C$_1$-C$_4$ alkyl,
into 6-carboxy-2-(3,5-dichlorophenyl)-6-benzoxazole of formula III,

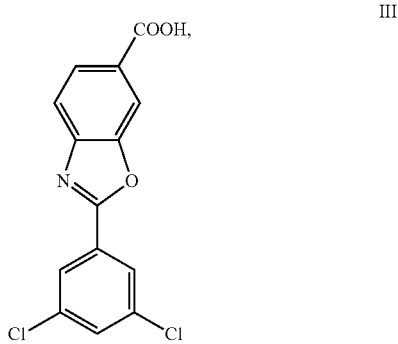 [SMILES: O=C(O)c1ccc2nc(-c3cc(Cl)cc(Cl)c3)oc2c1]

wherein step a) comprises the substeps of:
a1) treating the compound of formula II with a first inorganic base selected from the group consisting of sodium hydroxide and potassium hydroxide, in the presence of a first solvent or a first mixture of solvents to provide a compound of formula IIIa

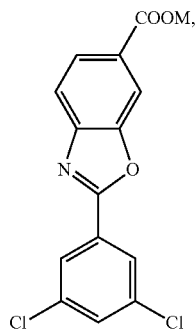

wherein M is a cation selected from the group consisting of sodium and potassium;

a2) treating the compound of formula IIIa obtained in substep a1) with an acid to provide 6-carboxy-2-(3,5-dichlorophenyl)-6-benzoxazole of formula III

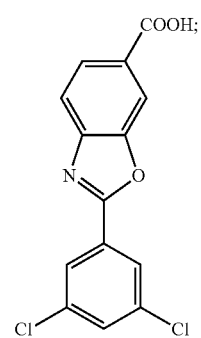

and b) converting 6-carboxy-2-(3,5-dichlorophenyl)-6-benzoxazole of formula III into 1-deoxy-1-methylamino-D-glucitol 2-(3,5-dichlorophenyl)-6-benzoxazolecarboxylate of formula I, wherein step b) comprises the substeps of:
  b1) adding N-methyl-D-glucamine to 6-carboxy-2-(3,5-dichlorophenyl)-6-benzoxazole of formula III obtained in step a),
  b2) removing the solvent of the resulting mixture obtained in substep b1), and
  b3) treating the resulting mixture obtained in substep b2) with a second solvent or a second mixture of solvents.

2. The process according to claim 1, wherein 6-carboxy-2-(3,5-dichlorophenyl)-6-benzoxazole of formula III is not isolated.

3. The process according to claim 1, wherein step a) comprises an additional substep a3) of adding water to the resulting mixture obtained after substep a2).

4. The process according to claim 3, wherein the amount of water added in substep a3) is of from 1:1 (v/w) to 10:1 (v/w) with respect to the weight of compound of formula II treated in substep a1).

5. The process according to claim 3, wherein step a) comprises an additional substep a4) of decanting the resulting mixture obtained in substep a3) and discarding the aqueous phase.

6. The process according to claim 1, wherein said first mixture of solvents used in substep a1) is a mixture of tetrahydrofuran and water.

7. The process according to claim 6, wherein the ratio of tetrahydrofuran to water is in the range of from 2:1 (v/v) to 15:1 (v/v).

8. The process according to claim 1, wherein substep a1) is conducted at a temperature of from 40° C. to 70° C.

9. The process according to claim 1, wherein substep a2) is conducted at a temperature of from 35° C. to 70° C.

10. The process according to claim 3, wherein substep a3) is conducted at a temperature of from 35° C. to 70° C.

11. The process according to claim 5, wherein substep a4) is conducted at a temperature of from 35° C. to 70° C.

12. The process according to claim 1, wherein R is selected from the group consisting of methyl and ethyl.

13. The process according to claim 1, wherein the cation M is sodium.

14. The process according to claim 1, wherein the mixture of solvents in b3) is a mixture of an alcohol and water.

15. The process according to claim 14, wherein the alcohol is selected from the group consisting of methanol, ethanol and isopropanol.

16. The process according to claim 14, wherein substeps b1), and/or b2) and/or b3) are conducted at a temperature of from 30° C. to 70° C.

17. A process according to claim 1, in which the compound of formula II

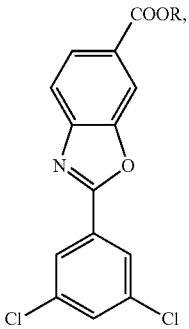

wherein R is a $C_1$-$C_4$ alkyl, is prepared by a process comprising the steps of:
  i) reacting a compound of formula V,

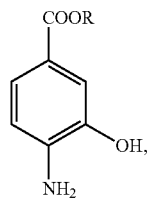

wherein R is as defined above, with a compound of formula VI,

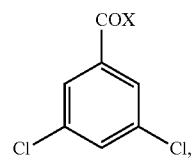

wherein X is a leaving group in the presence of a second inorganic base and in a third solvent or a third mixture of solvents to provide a compound of formula IV,

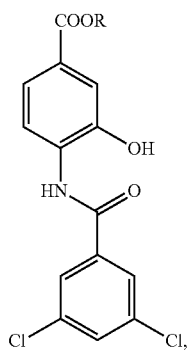

IV wherein R is as defined above; and
ii) converting the compound of formula IV into the compound of formula II.

18. The process according to claim 17, wherein R is selected from the group consisting of methyl and ethyl.

19. The process according to claim 17, wherein said second inorganic base is an alkali metal carbonate or bicarbonate.

20. The process according to claim 17, wherein said third solvent is tetrahydrofuran or wherein said third mixture of solvents comprises tetrahydrofuran.

21. A compound of formula IIIa,

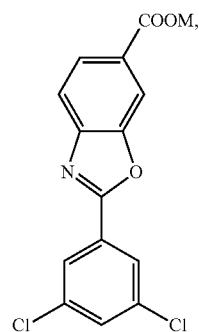

IIIa wherein M is selected from the group consisting of sodium and potassium.

22. A process for preparing a pharmaceutical composition comprising 1-deoxy-1-methylamino-D-glucitol 2-(3,5-dichlorophenyl)-6-benzoxazolecarboxylate of formula I, said process comprising the process according to claim 1 to obtain 1-deoxy-1-methylamino-D-glucitol 2-(3,5-dichlorophenyl)-6-benzoxazolecarboxylate of formula I, and further combining said 1-deoxy-1-methylamino-D-glucitol 2-(3,5-dichlorophenyl)-6-benzoxazolecarboxylate of formula I with at least one pharmaceutically acceptable carrier or excipient.

* * * * *